United States Patent [19]
Johnson et al.

[11] Patent Number: 5,483,546
[45] Date of Patent: Jan. 9, 1996

[54] SENSOR SYSTEM FOR REMOTE SPECTROSCOPY

[75] Inventors: Bernadette Johnson, Hollis, N.H.; John J. Zayhowski, Pepperell, Mass.

[73] Assignee: Massachusetts Institute of Technology, Cambridge, Mass.

[21] Appl. No.: 240,982

[22] Filed: May 11, 1994

Related U.S. Application Data

[63] Continuation-in-part of Ser. No. 206,124, Mar. 4, 1994, Pat. No. 5,394,413, which is a continuation-in-part of Ser. No. 193,781, Feb. 8, 1994, abandoned.

[51] Int. Cl.[6] .................................................. H01S 3/11
[52] U.S. Cl. ............................ 372/10; 372/22; 356/318
[58] Field of Search ........................ 372/10, 22; 359/328; 356/318; 250/227.23

[56] References Cited

U.S. PATENT DOCUMENTS

| | | | |
|---|---|---|---|
| 3,788,742 | 1/1974 | Garbuny | 356/342 |
| 4,723,257 | 2/1988 | Baer et al. | 372/108 |
| 4,827,121 | 5/1989 | Vidrine, Jr. et al. | 250/227 |
| 5,049,738 | 9/1991 | Gergely et al. | 250/301 |
| 5,054,878 | 10/1991 | Gergely et al. | 250/572 |
| 5,084,617 | 1/1992 | Gergely | 250/253 |

OTHER PUBLICATIONS

Chen, Y. C., et al., "Self-Stabilized Single-Longitudinal-Mode Operation in a Self-Q-Switched Cr,Nd:YAG Laser," *Optics Letters*, 18(17):1418–1419 (1993, Sep.).

Chudyk, W., et al., "Dynamic Range Limits in Field Determination of Fluorescence Using Fiber Optic Sensors," *Chemical, Biochemical, and Environmental Fiber Sensors II*, SPIE vol. 1368 Jan. (1990).

*Primary Examiner*—Rodney B. Bovernick
*Assistant Examiner*—Robert E. Wise
*Attorney, Agent, or Firm*—Hamilton, Brook, Smith & Reynolds

[57] ABSTRACT

A sensing system for high sensitivity spectroscopic measurements is described. An optically pumped passively Q-switched laser emits laser light of a first frequency at a sensing site. Frequency-converting crystals coupled to the laser convert the laser output to light of a second frequency which illuminates the sensing site and produces a return radiation that is characteristic of the material at the site. A pump source coupled to the laser by an optical fiber pumps the laser with light of a third frequency that is efficiently propagated over the fiber. A sensor senses the radiation returning from the sensing site. The sensor is either an optical detector located at the site or an optical fiber having one end located at the site and the other end coupled to a remote optical detector.

22 Claims, 2 Drawing Sheets

SENSOR SYSTEM FOR REMOTE SPECTROSCOPY

GOVERNMENT SUPPORT

The Government has rights in this invention pursuant to Contract Number F 19628-90-C-0002, awarded by the United States Department of the Air Force.

RELATED APPLICATIONS

This application is a continuation-in-part of U.S. application Ser. No. 08/206,124, now U.S. Pat. No. 5,394,413, filed Mar. 4, 1994 which is a continuation-in-part of application Ser. No. 08/193,781 now abandoned, filed Feb. 8, 1994, each of which is incorporated in its entirety by reference herein.

BACKGROUND OF THE INVENTION

Optical techniques such as single wavelength transmission, differential absorption, laser-induced fluorescence and stimulated Raman scattering are typically used to provide quantitative measurements of soil, water and air contaminants. In recent years, the ability of these optical techniques to provide remote measurements has been facilitated by using optical fibers coupled to lasers operating at wavelengths selected to provide high measurement sensitivity. For many applications, the optimum wavelengths for high measurement sensitivity lie in the UV to visible region of the spectrum. Unfortunately, because of excessive attenuation, it is difficult to propagate the optimal measurement wavelengths very far in commercially available optical fibers. This limitation has restricted remote fiber-based sensor systems to either short ranges, i.e., a few meters, when operating at UV wavelengths or to long ranges at non-optimal measurement wavelengths.

A need exists, therefore, for a remote fiber-based sensor system that can efficiently operate over long distances while retaining the high measurement sensitivity of UV light.

SUMMARY OF THE INVENTION

The present invention provides a remote sensing apparatus and method for satisfying the aforementioned need. The sensor system of the present invention achieves high measurement sensitivity by converting, at a sensing site, laser output of a first frequency to light of a second frequency (UV light). The laser light of the first frequency is generated from light of a third frequency from a remote pump source which is used to pump the laser. Light of the third frequency is one that can be efficiently propagated over an optical fiber to the sensing site.

The laser output at the first frequency is converted to the second frequency using nonlinear optics. The laser is preferably a passively Q-switched microlaser of the type described in the aforementioned patent application Ser. No. 08/206,124. The passively Q-switched microlaser has the advantage over other laser sources of eliminating the need for electrical power at the remote site. The passively Q-switched microlaser produces pulses of such short duration (e.g., of the order of or less than 1 ns) as to allow for measurement of fluorescence lifetimes.

The sensor system of the invention generally comprises a laser head in the form of a passively Q-switched microlaser and a frequency converter coupled to the laser for converting the laser output to a higher frequency at a sensing site. The sensor system also comprises a pump source coupled to the laser by an optical fiber for pumping the laser at a frequency that propagates efficiently over the fiber, and a sensor for sensing radiation attenuated, emitted, scattered, or dispersed at the sensing site. The frequency converter comprises one or more nonlinear optical crystals selected for their frequency conversion characteristics. The output of the frequency converter illuminates the sensing site and produces a return radiation that is characteristic of the material at the sensing site. The sensor can be an optical detector in proximity to the sensing site or an optical fiber having one end in proximity to the sensing site and the other end coupled to a remote optical detector.

By locating the pump source and laser head at opposite ends of an optical fiber, the invention takes advantage of the high transmissivity of optical fiber for near-infrared radiation and produces UV radiation only at the sensing site, which can be hundreds of meters or even kilometers from the pump source. The high measurement sensitivity over long distances provided by the invention is useful in monitoring materials in air, soil and water environments. Applications include, for example, subterranean leak mapping of buried fuel tanks, groundwater monitoring, smokestack effluent monitoring, industrial process control, and hazardous waste characterization. The principles of the invention can also be applied to provide multiple sensing elements by coupling a multi-element diode array through optical fibers to many individual laser heads. Further, multi-element sensing systems in accordance with the invention can be constructed that have different UV excitation wavelengths to achieve a sensing system with greatly enhanced chemical selectivity. The high measurement sensitivity over long distances of the invention also allows such a multi-element sensing system to monitor a large area from a centrally located remote site.

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
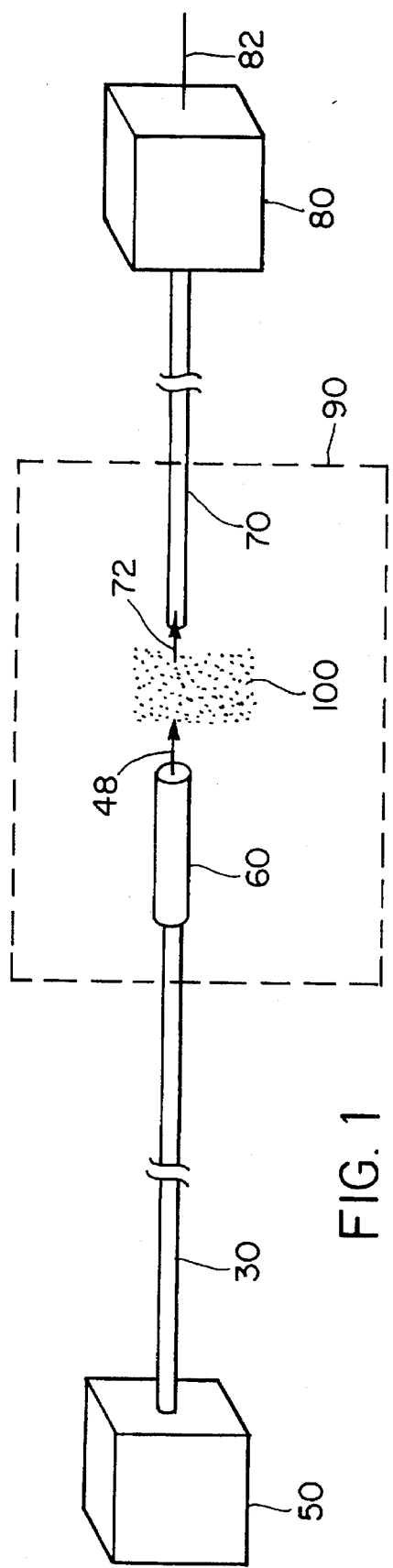
FIG. 1 is a schematic perspective view of a sensor system embodying the present invention wherein return radiation is propagated over an optical fiber to an optical detector.

A remote sensing system in accordance with the invention will now be described in detail in connection with the schematic perspective view in FIG. 1. The remote sensing system is comprised in general of an optical pump source 50, an optical fiber 30, a laser head 60, an optical fiber 70, and an optical detector 80. Pump source 50, which can be a single pump diode or a multi-element diode array, is coupled to optical fiber 30 and produces light at a frequency that can be efficiently propagated over optical fiber 30. A typical wavelength for the pump source is in the near-infrared region, for example, 808 nm. Optical fiber 30 couples pump light into laser head 60 which provides light output 48 to illuminate the material 100 at a sensing site 90. One end of optical fiber 70 is located in proximity to laser head 60 at sensing site 90 and receives return radiation 72 which is emitted, scattered, or dispersed from material 100 illuminated by light output 48. Return radiation 72 has a frequency spectrum and amplitude that is characteristic of material 100. Return radiation 72 propagates over fiber 70 to optical detector 80 coupled to the opposite end of optical fiber 70. Optical detector 80 provides an electrical signal 82 indicative of the amplitude and frequency spectrum of return radiation 72.

Figure 2:
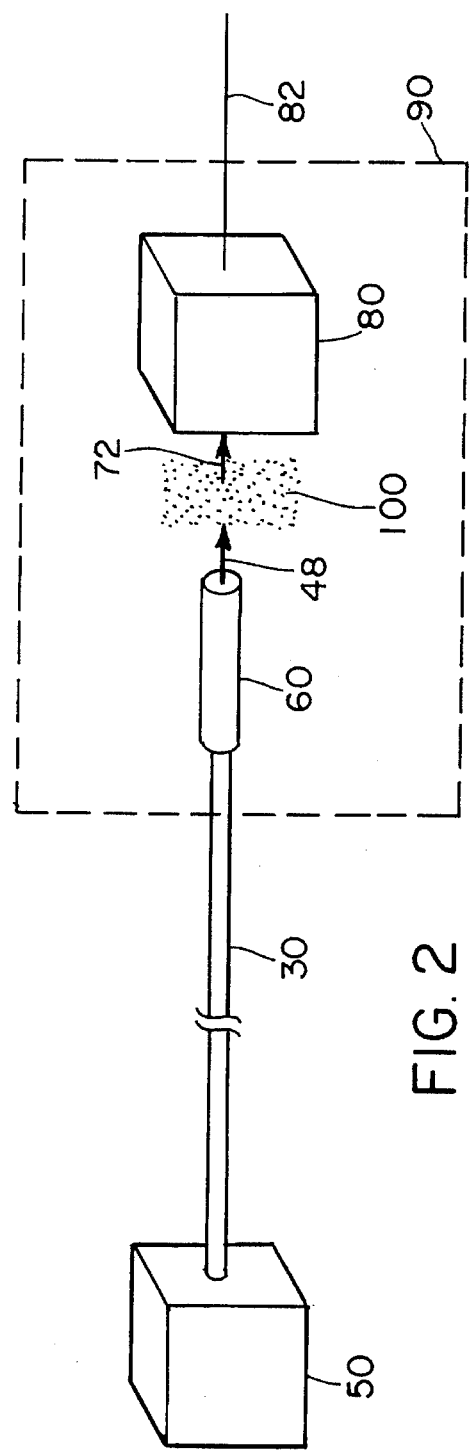
FIG. 2 is a schematic perspective view of an alternative embodiment of the sensor system wherein return radiation is directly detected by an optical detector.

FIG. 2 shows an alternative embodiment of the remote sensing system, wherein optical detector 80 is located at sensing site 90 and directly senses return radiation 72 to provide an electrical signal 82 indicative of the amplitude and frequency spectrum of return radiation 72.

Figure 3:
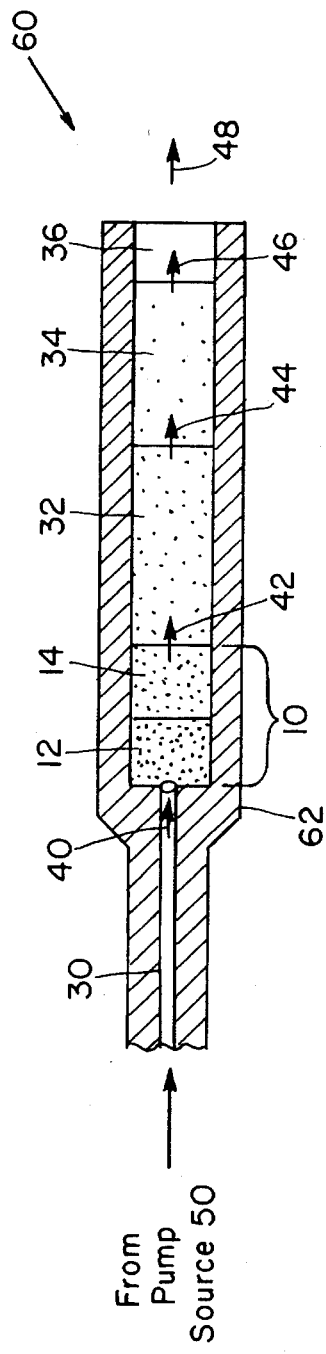
FIG. 3 is a schematic sectional view of a preferred embodiment of a laser head according to the present invention.

Referring to FIG. 3, a preferred embodiment of the laser head 60 comprises a cylindrical housing 62 enclosing a passively Q-switched microlaser 10, frequency-doubling crystals 32 and 34, and an output window 36. A preferred laser head configuration is approximately 1 cm in diameter and 3 cm long. Optical fiber 30 couples pump light 40 to passively Q-switched microlaser 10. An embodiment of passively Q-switched microlaser 10 comprises a short piece of gain medium 12, for example $Nd^{3+}$:YAG, bonded to a saturable-absorber crystal 14, for example $Cr^{4+}$:YAG. A frequency-doubling crystal 32, for example KTP(K-$TiOPO_4$), is disposed in the path of the laser output 42 and generates output 44 at the second harmonic of the oscillating frequency. A second frequency-doubling crystal 34, for example BBO ($\beta$-$BaB_2O_4$), is placed adjacent to the first frequency-doubling crystal 32. The output 44 of the first frequency-doubling crystal 32 passes through the second frequency-doubling crystal 34 and is transformed into output 46 at the fourth harmonic of the laser output 42. The output 46 passes through window 36 to provide output 48. With this embodiment, pump source 50, transmitted over optical fiber 30, may be converted by passively Q-switched microlaser 10 into laser light 42, which is subsequently quadrupled in frequency by the frequency-doubling crystals 32 and 34 into ultraviolet light 48, which could not be efficiently transmitted using currently available fibers. Thus, ultraviolet light 48 may be generated several kilometers away from a pump source 50, at the opposite end of an optical fiber 30.

The embodiment of FIG. 3 may be made more efficient by disposing conditioning optics, such as a graded index (GRIN) lens, between microlaser 10 and frequency-doubling crystal 32 to improve the doubling efficiency. Similarly, a GRIN lens could be disposed between the frequency-doubling crystals 32 and 34 to further improve the doubling efficiency. Thus, an increase in the amount of UV radiation generated may be achieved with only a minimal increase in the size and complexity of the laser head.

Figure 4:
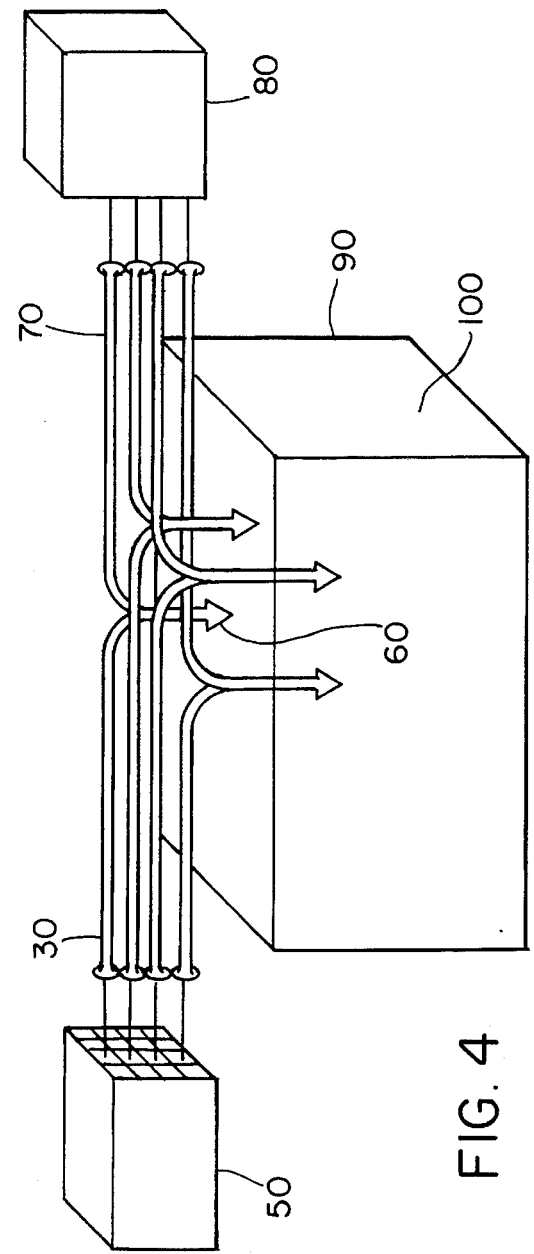
FIG. 4 is a schematic perspective view of an alternative embodiment of the sensor system wherein the pump source is a multi-element diode array connected to a plurality of fibers.

FIG. 4 illustrates an embodiment of a sensor system of the present invention wherein a multi-element diode array 50 is used to pump several laser head 60 elements over fibers 30 that are embedded in the material 100 at the sensing site 90. For each laser head 60, detection of the emitted radiation occurs via a second fiber 70 which is then directed to an optical detector 80. The optical detector 80 can be a compact two-dimensional spectrometer, for example, which can then provide a large number of high-resolution, large dynamic range spectra measurements.

To illustrate the capabilities of a sensor system according to the present invention, consider first the sensitivity of existing UV fiber-based sensor systems that operate over short fibers. As an example, a system developed to provide in situ monitoring of unleaded fuel concentrations in soil used laser-induced fluorescence from a frequency-quadrupled Nd:YAG laser coupled to an optical fiber. The laser delivered approximately 10 µJ per pulse at 0.5 Hz repetition rate to the proximal end of a 10 m fiber; attenuation in the fiber was about 0.7 dB/m, which resulted in approximately 2 µJ of laser energy at the remote end of the fiber. To deliver the same pulse energy over a 100 m fiber would require a UV pulse energy of 20 J at the laser source. Such a large amount of energy would greatly increase the laser requirements and cannot likely be propagated over commercially available optical fibers.

In contrast, consider a system where CW near-infrared light is propagated over an optical fiber 10 meters in length to a laser head comprising a passively Q-switched microlaser and two frequency doubling crystals. Estimates show that approximately 1 W of pump light at 808 nm wavelength transmitted over the fiber in accordance with the invention can produce laser head output of 1 µJ per pulse at 266 nm. To obtain the same pulse energy in the same manner over a 100 meter fiber requires only a small increase in pump light to approximately 1.25 W.

Thus, the present invention takes advantage of the low attenuation of fiber at 808 nm ($\approx$0.1 dB/m) such that pump power requirements change minimally even when the fiber length is increased to hundreds of meters.

While this invention has been particularly shown and described with references to preferred embodiments thereof, it will be understood by those skilled in the art that various changes in form and detail may be made therein without departing from the spirit and scope of the invention as defined by the appended claims.

What is claimed is:

1. A system for sensing characteristics of a material at a site comprising:
   a) an optically pumped laser at the site for emitting laser light of a first frequency;
   b) a frequency converter coupled to the laser for converting the laser light emitted by the laser to light of a second frequency in the UV range such that the site is illuminated with light of the second frequency to produce a return radiation characteristic of the material;
   c) a pump source remote from the laser for pumping the laser with radiation of a third frequency;
   d) an optical fiber for coupling the radiation of the third frequency to the laser; and
   e) a sensor for sensing the return radiation at the site.

2. The system of claim 1 wherein the optical fiber is coupled to the laser without intermediate focusing optics.

3. The system of claim 1 wherein the sensor comprises an optical detector in proximity to the site.

4. The system of claim 1 wherein the sensor comprises a second optical fiber having a first end in proximity to the site and a second end coupled to an optical detector.

5. The system of claim 1 wherein the laser comprises an optically pumped passively Q-switched microlaser.

6. The system of claim 1 wherein the third frequency is in the near-infrared range.

7. The system of claim 1 wherein the frequency converter comprises nonlinear optical crystals selected from the group including KTP and BBO.

8. The system of claim 1 wherein the pump source comprises a multi-element diode-pump array.

9. A sensing apparatus comprising:
  a) an optically pumped passively Q-switched microlaser for emitting laser light of a first frequency for location in proximity to a sensing site;
  b) a frequency converter coupled to the laser for converting the laser light emitted by the laser to light of a second frequency in the UV range such that the sensing site is illuminated with light of the second frequency and produces a return radiation which is a function of the properties of the site;
  c) a pump source coupled to the laser by an optical fiber for pumping the laser with pump light of a third frequency which is efficiently propagated over the fiber; and
  d) a sensor for sensing the return radiation at the sensing site.

10. The sensing apparatus of claim 9 wherein the sensor comprises an optical detector in proximity to the site.

11. The sensing apparatus of claim 9 wherein the sensor comprises a second optical fiber having a first end in proximity to the site and a second end coupled to an optical detector.

12. A method for sensing characteristics of material at a site comprising the steps of:
  a) emitting laser light of a first frequency from an optically pumped laser at the site;
  b) coupling a frequency converter to the laser for converting the laser light emitted by the laser to light of a second frequency in the UV rang, such that the site is illuminated with light of the second frequency to produce a return radiation characteristic of the material;
  c) pumping the laser with radiation of a third frequency from a pump source;
  d) coupling the radiation of the third frequency to the laser with an optical fiber; and
  e) sensing the return radiation at the site with a sensor.

13. The method of claim 12 wherein the optical fiber is coupled to the laser without intermediate focusing optics.

14. The method of claim 12 wherein the sensor comprises an optical detector in proximity to the site.

15. The method of claim 12 wherein the sensor comprises a second optical fiber having a first end in proximity to the site and a second end coupled to an optical detector.

16. The method of claim 12 wherein the laser comprises an optically pumped passively Q-switched microlaser.

17. The method of claim 12 wherein the third frequency is in the near-infrared range.

18. The method of claim 12 wherein the frequency converter comprises nonlinear optical crystals selected from the group including KTP and BBO.

19. The method of claim 12 wherein the pump source comprises a multi-element diode-pump array. A method of sensing, comprising the steps of:

20. A method of sensing, comprising the steps of:
  a) pumping optically a passively Q-switched microlaser for emitting laser light of a first frequency for location in proximity to a sensing site;
  b) coupling a frequency converter to the laser for converting the laser light emitted by the laser to light of a second frequency in the UV range such that the sensing site is illuminated with light of the second frequency and produces a return radiation which is a function of the properties of the site;
  c) coupling a pump source to the laser by an optical fiber for pumping the laser with pump light of a third frequency which is efficiently propagated over the fiber; and
  d) sensing the return radiation at the sensing site with a sensor.

21. The method of claim 20 wherein the sensor comprises an optical detector in proximity to the site.

22. The method of claim 20 wherein the sensor comprises a second optical fiber having a first end in proximity to the site and a second end coupled to an optical detector.

* * * * *

UNITED STATES PATENT AND TRADEMARK OFFICE
CERTIFICATE OF CORRECTION

PATENT NO. : 5,483,546
DATED : January 9, 1996
INVENTOR(S) : Bernadette Johnson and John J. Zayhowski It is certified that error appears in the above-identified patent and that said Letters Patent is hereby corrected as shown below:

Column 5, line 42, delete "rang" and insert
---range---.

Column 6, lines 19-20, after "array." delete "A method of sensing, comprising the steps of:".

Signed and Sealed this

Twenty-third Day of April, 1996

Attest:

BRUCE LEHMAN

Attesting Officer    Commissioner of Patents and Trademarks